United States Patent
Schmidt

(10) Patent No.: US 9,925,017 B2
(45) Date of Patent: Mar. 27, 2018

(54) MEDICAL NAVIGATION IMAGE OUTPUT COMPRISING VIRTUAL PRIMARY IMAGES AND ACTUAL SECONDARY IMAGES

(75) Inventor: Robert Schmidt, Munich (DE)

(73) Assignee: Brainlab AG, Munich (DE)

( * ) Notice: Subject to any disclaimer, the term of this patent is extended or adjusted under 35 U.S.C. 154(b) by 897 days.

(21) Appl. No.: 12/750,742

(22) Filed: Mar. 31, 2010

(65) Prior Publication Data

US 2010/0295931 A1 Nov. 25, 2010

Related U.S. Application Data

(60) Provisional application No. 61/165,551, filed on Apr. 1, 2009.

(30) Foreign Application Priority Data

Mar. 31, 2009 (EP) ..................................... 09156927

(51) Int. Cl.

| H04N 7/18 | (2006.01) |
|---|---|
| A61B 90/00 | (2016.01) |
| A61B 34/20 | (2016.01) |
| A61B 1/04 | (2006.01) |
| A61B 1/05 | (2006.01) |

(Continued)

(52) U.S. Cl.
CPC .............. *A61B 90/36* (2016.02); *A61B 34/20* (2016.02); *A61B 1/041* (2013.01); *A61B 1/042* (2013.01); *A61B 1/05* (2013.01); *A61B 1/0638* (2013.01); *A61B 1/07* (2013.01); *A61B 5/06* (2013.01); *A61B 2090/364* (2016.02); *A61B 2090/365* (2016.02); *G02B 21/365* (2013.01); *H04N 2005/2255* (2013.01)

(58) Field of Classification Search
USPC ............... 348/65, 77, 68, 73, 69, 71, 76, 79; 600/109, 101, 117, 118, 160, 178, 112
See application file for complete search history.

(56) References Cited

U.S. PATENT DOCUMENTS

| 4,962,463 A * | 10/1990 | Crossno ..................... G06F 3/14 715/201 |
|---|---|---|
| 5,749,362 A | 5/1998 | Funda et al. |

(Continued)

FOREIGN PATENT DOCUMENTS

| DE | 196 39 615 | 4/1998 |
|---|---|---|
| EP | 0 685 088 | 9/2000 |

(Continued)

*Primary Examiner* — Shawn An
(74) *Attorney, Agent, or Firm* — Tucker Ellis LLP

(57) ABSTRACT

The invention relates to an image output method for medical navigation in which the positional relationship of an instrument with respect to a part of a patient's body is ascertained, and in which the instrument and the part of the patient's body are displayed in the correct positional relationship on an image output, wherein the display of the part of the patient's body is based on the one hand on virtual image data captured by means of a medical imaging method and on the other hand on actual images captured during navigation, wherein the virtual image data is displayed on the image output primarily and as the basis of the image, and the actual images are superimposed on it merely as an addition and secondarily. It also relates to an image generating and image output device for medical navigation.

24 Claims, 1 Drawing Sheet

(51) Int. Cl.
*A61B 1/06* (2006.01)
*A61B 5/06* (2006.01)
*A61B 1/07* (2006.01)
*G02B 21/36* (2006.01)
*H04N 5/225* (2006.01)

(56) References Cited

U.S. PATENT DOCUMENTS

| | | | | |
|---|---|---|---|---|
| 5,765,561 | A * | 6/1998 | Chen | A61B 19/52 348/77 |
| 6,231,526 | B1 | 5/2001 | Taylor et al. | |
| 6,757,416 | B2 * | 6/2004 | Kleiman | A61B 5/055 382/103 |
| 6,815,659 | B2 * | 11/2004 | Cartlidge | G02B 13/00 250/208.1 |
| 8,027,526 | B2 * | 9/2011 | Boese | A61B 6/032 378/8 |
| 2002/0075201 | A1 | 6/2002 | Sauer et al. | |
| 2002/0082498 | A1 | 6/2002 | Wendt et al. | |
| 2005/0054897 | A1 * | 3/2005 | Hashimoto | A61B 5/0031 600/118 |
| 2005/0143651 | A1 * | 6/2005 | Verard | A61B 19/52 600/424 |
| 2007/0183637 | A1 * | 8/2007 | Kreuzer | A61B 6/481 382/128 |
| 2007/0238981 | A1 | 10/2007 | Zhu et al. | |
| 2008/0183068 | A1 * | 7/2008 | Carls | A61B 5/04001 600/411 |
| 2008/0281989 | A1 * | 11/2008 | Hager | A61B 19/52 710/1 |
| 2011/0013008 | A1 * | 1/2011 | Nagamachi | A61B 5/0059 348/79 |

FOREIGN PATENT DOCUMENTS

| EP | 1 321 105 | 6/2003 |
|---|---|---|
| EP | 1913893 | 7/2003 |

\* cited by examiner

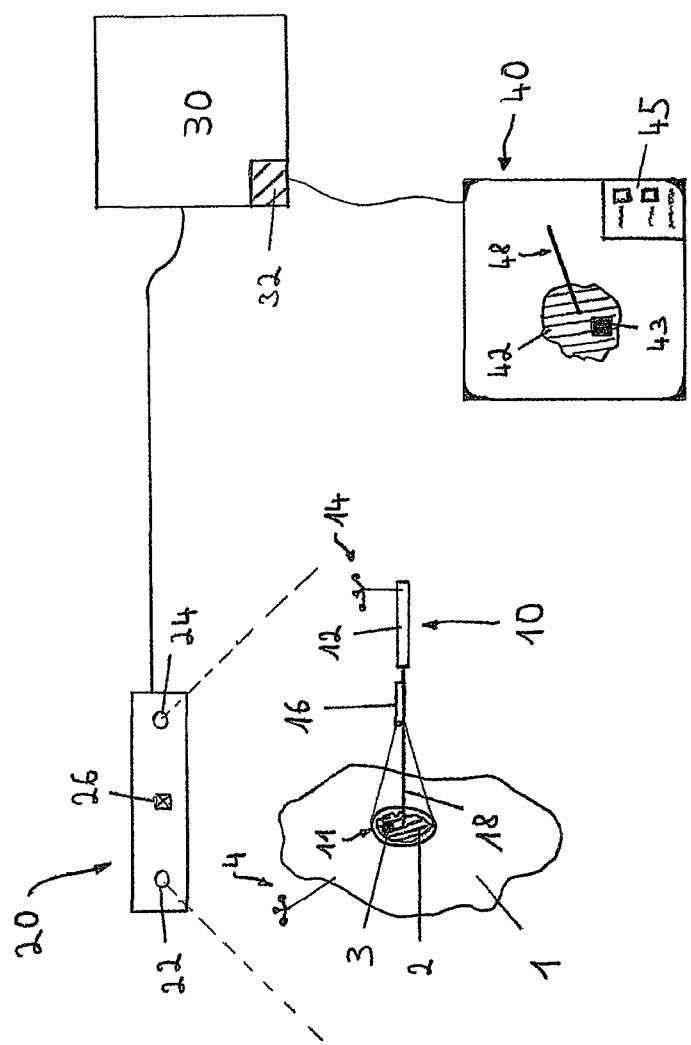

MEDICAL NAVIGATION IMAGE OUTPUT COMPRISING VIRTUAL PRIMARY IMAGES AND ACTUAL SECONDARY IMAGES

RELATED APPLICATION DATA

This application claims the priority of U.S. Provisional Application No. 61/165,551, filed on Apr. 1, 2009, which is hereby incorporated in its entirety by reference.

FIELD OF THE INVENTION

The invention relates to the technical field of medical navigation image output. Medical navigation is used within the framework of image-guided surgery and assists surgeons in optimally positioning their instruments, wherein for example reference is made to patient image data acquired beforehand. As a result, the physician performing the treatment is assisted by an image output, for example a monitor, on which they can identify where their instrument or its functional portion is situated in relation to particular parts of a patient's body—regions of interest. This technology is specifically advantageous in minimally invasive types of treatment, in which instruments are for example introduced through small openings in the surface of the patient's skin and in which with the aid of navigation, it becomes possible to identify where the instruments are situated relative to particular regions of interest on the patient, medical image data of which has been captured beforehand (CT, MR, x-ray images, ultrasound, PET).

BACKGROUND OF THE INVENTION

Such a navigation technique has for example been described in principle in DE 196 39 615 C2.

Combining transillumination and/or tomographic image capture image data and video images and/or actual images is also already known in principle, for example from EP 1 321 105 B1 or EP 0 685 088 B1 and from superimposing virtual image material in images of surgical microscopes. In these conventional image output methods, guidance is performed primarily on the basis of the data which can be visually captured, i.e. primarily on the basis of a "visual reality", while "virtual image data"—i.e. image data from medical imaging methods performed beforehand or during navigation—serves only as a second source of information, i.e. as a secondary, supplementary image data source. Thus, in accordance with the prior art, the image which can be captured visually, i.e. by the human eye or by the human eye with the assistance of cameras or object lenses, is merely augmented with the aid of the imaging data (CT, MR, x-ray, etc.), which incurs a number of disadvantages. In addition to the relatively marginal utilization of the virtual image material, access to the region of interest has to be uncovered when using a microscope, which makes the method more significantly invasive. If an endoscope is used, this forms a second instrument which additionally has to be controlled and checked and which in principle can also disrupt the freedom of movement of the treatment instrument.

SUMMARY OF THE INVENTION

It is therefore the object of the present invention to improve the image output in medical navigation such that available image information is optimally used. The intention is in particular also to improve the ergonomics in navigation methods and/or to minimize invasiveness.

This object is solved by a method in accordance with claim 1 and by a device in accordance with claim 16. The sub-claims define preferred embodiments of the invention.

The image output method for medical navigation in accordance with the invention is of the type in which the positional relationship of an instrument with respect to a part of a patient's body is ascertained, and the instrument and the part of the patient's body are displayed in the correct positional relationship on an image output, wherein the display of the part of the patient's body is based on the one hand on virtual image data captured by means of a medical imaging method and on the other hand on actual images captured during navigation. In accordance with the invention, the virtual image data is displayed on the image output primarily and as the basis of the image, and the actual images are superimposed on it merely as an addition and secondarily.

In other words, the present invention simply reverses the previously known assembly of the image data for the image output. Navigation assistance is performed primarily on the basis of the virtual data, whereby the invention uses a technological trend, for it is possible to generate increasingly better (i.e. realistic) three-dimensional data and to process it increasingly faster and better in real time, because the corresponding data-processing hardware is becoming increasingly faster. This results in highly realistic and detailed virtual image outputs. The visual reality, i.e. actual images as perceived by the human eye, is correlated—as a second and merely augmentative form of image information—with the virtual image data and output together with it in accordance with the requirements and wishes of the user. Using such a technique in accordance with the invention, it is for example possible to more easily confirm positions of instruments when they are displayed against a less complex virtual data situation, i.e. when for example the virtual data is reduced to a particular level, such that unnecessary information is removed. Additional anatomical insights (live video) can also be provided with regard to the interactions of instruments.

Other fundamental advantages lie in the fact that it is possible to work less invasively, because the base navigation information—i.e. the virtual image data—actually already contains all the information about the "interior" of the patient, hence little direct viewing access has to be provided. In specific embodiments, the number of instruments can be reduced, and pre-operative and/or intra-operative virtual data can be updated in accordance with the interactions of the instruments.

In accordance with one embodiment of the present invention, the virtual image data can be weighted more heavily than the actual images when assembling the output image, such that the navigation-assisting information provided from the images, which is based on virtual image data, constitutes more than 50%, in particular more than 70%, specifically more than 90% and up to 99.9%. The weighting will be dependent on the respective application.

The virtual image data can comprise image data which is captured before or during navigation by means of computed tomography, magnetic resonance tomography, an x-ray recording or fluoroscopic recording, a PET or SPECT recording or another medical imaging method. The actual images can be images which can be visually captured, in particular images which correspond to an actual view of a region of interest or which directly image reality, because they comprise images which are implemented specifically by video capture apparatuses or by an object lens and are captured in real time. The term "actual images" refers to all images such as can be seen by the human eye and/or by the human eye with the assistance of for example a camera or object lens. They come from the object and/or part of the patient's body being observed itself and not—like the virtual image data—from a data set for the part of the patient's body.

If a division into a primary basis of the image and a secondary basis of the image is maintained in accordance with the invention and/or a corresponding weighting is performed, the actual images can also in principle be provided by microscopes or endoscopes in the present invention.

In a preferred embodiment of the invention, the actual images are provided by a video image capture unit, in particular a camera or a camera light recorder (object lens or optical fiber end), wherein said video image capture unit is arranged on an instrument which is in particular a medical treatment instrument, specifically a pointer, a coagulation instrument, a pair of tweezers, a scalpel or a clamp. In these embodiments in particular, a reduction in the number of instruments results.

Preferably, the instrument which is navigated in accordance with the invention is specifically equipped for said navigation and can in particular be positionally detected by means of a tracking system, which can be realized by providing a tracking reference. It can also be provided as a pre-calibrated instrument, i.e. as an instrument for which the geometry is known beforehand and stored in the navigation system and which can therefore be unambiguously identified and navigated directly, without pre-calibration. It can use a plurality of instruments which are each provided with a video image capture unit, wherein the actual image data thus obtained is used to reciprocally observe or monitor the instruments and/or to produce supplementary images. Disruptive interactions can thus be avoided. Using the video image capture unit, it is also possible to detect non-visible light wavelengths which are then used for image optimization.

It is possible to use the combination of the virtual image data and the actual images in order to positionally register the virtual image data, in particular for elastic image data registration (morphing). This combination can also be used for updating the virtual image data. The image material for assembling the image to be output, i.e. the image information, can be tested for relevance (and weighted) in the navigation system or by a specialized separate computer unit, wherein less important image constituents are omitted from the image and/or more important image constituents are intensified or highlighted in the image. This can also be controlled by the user, upon an input by the user.

The invention also relates to a program which, when it is running on a computer or is loaded on a computer, causes the computer to perform a method such as is described here in various embodiments. It also relates to a computer program storage medium comprising such a program.

The invention can comprise any of the features described here, in any expedient combination or also individually. It can be regarded in particular as a method, but can also—as in claim 16—be interpreted as a device. The use of the method features or device features detailed here, within the framework of producing image during medical navigation, is likewise part of the present invention.

BRIEF DESCRIPTION OF THE DRAWING

The one enclosed FIGURE schematically shows an embodiment which implements the present invention.

DETAILED DESCRIPTION

In the FIGURE, the reference sign 1 indicates—in a highly schematized form—a part of a patient's body which comprises a region of interest 2 in which a navigation-assisted treatment is to be performed. Tissue situated in the region of interest 2 has been examined beforehand using medical imaging, and a virtual data set of said tissue has been produced (for example using a magnetic resonance and/or magnetic resonance method). This tissue is indicated by hatching. An object which can be visually captured particularly easily is also imaged in the region of interest 2 and bears the reference sign 3.

A reference array 4 is situated on the part of the patient's body. This reference array 4 and a reference array on the surgical instrument 10 (likewise shown) are situated in the visual range of a tracking system 20 which positionally detects and tracks these reference arrays 4 and 14 using two cameras 22 and 24, such that where the instrument 10 and the part of the body 1 are situated is known at any time. The tracking system 20 emits infrared pulses via the infrared transmitter 26 which are reflected by marker spheres on the tracking references 4, 14.

Using the instrument 10, which can be operated via the grip 12 and comprises an instrument tip 18, a surgeon can work in the region of interest 2, even minimally invasively through a very small body opening, because the surgeon is provided with the image data concerning the positioning of the tip 18 of his/her instrument and the tissue in the region of interest 2, on an image output 40, as a tissue image 42 and a tip image 48.

Images are generated and the image output controlled, together with the required calculation of the position, with the aid of a navigation system 30 which is only schematically shown and in which one part, as a "black box", is indicated as the image display control 32. Using this image display control 32, it is for example possible to influence how virtual image data is used as primary and fundamental image data, and actual images are only used secondarily. Other controls can for example be performed on the image output 40 itself, possibly—as shown—via a touch screen panel 45 due to inputs by the user of the system. The virtual image data is stored in the navigation system 30, and the position data is obtained by the navigation system 30 from the tracking system 20. It also, however, obtains other information, namely the secondary actual image data for producing the image on the image output 40, which in the present example embodiment is generated by a video camera which is seated on the instrument tip 18 and has been provided with the reference sign 16. Said camera has a field of view 11; it can take an image of the entire region of interest 2, but in particular of the object 3.

Unlike the previous embodiments according to the prior art, however, the image 42 of the region of interest is not primarily established by the image of the camera 16 (which can be transmitted by radio or cable to the navigation system 30), since—as the present invention has identified—the virtual image material, i.e. the virtual image data from the magnetic resonance tomography produced beforehand, is more suitable for this purpose. The image 43 of the object can however be "added into" the image output 40, from the image material which comes from the camera 16 and, in the case of the object 3, may even provide a better or more up-to-date image. The image 43 of the object is thus a secondary image in a navigation which is otherwise based on the primary, virtual tissue image data 42.

In the following, reference is also made to possible embodiments of the invention: a surgical instrument, for example a pair of tweezers for tumor ablation or a Blakesley clamp for removing soft tissue, which has been calibrated for navigation is equipped with a miniaturized video camera for real-time image recording, wherein the field of view of the camera observes the interactions between the surgical instrument and the more immediate environment. Optionally, for example with the aid of optical filters and/or light sources, the camera expands the light wavelengths which can be used for the user. The camera can for example detect fluorescent ultraviolet dyes which indicate a cortical bloodstream, tumor boundaries, et al. Selecting wavelengths and/or using specific wavelengths can likewise be used to absorb or eliminate unnecessary information (for example, blood on the camera lens).

If more than one instrument is used, cameras which are arranged on each instrument or on a number of instruments can be used to provide video monitoring for the instruments, in order to ensure that the instruments do not come into conflict and/or collide with each other. Another possible use is to use the video images together with the corresponding 3D positions for elastic image registration, wherein the video images can augment low-quality intra-operative image data (for example, ultrasound) with additional information, in order to provide a better starting point for algorithms which perform image registrations (morphing).

In accordance with the invention, the region of interest can be localized with navigation guidance, wherein the video images continuously augment the virtual image data along the incision path and are for example transparently superimposed in order to enable better anatomical comprehension and a visual confirmation of the anticipated positions of instruments.

If the instrument is situated in the region of interest, it can still be positioned with navigation guidance, and the anticipated navigation position can still be visually confirmed, but the system in accordance with the invention additionally offers the option of observing the interactions of the instrument (with other instruments or its immediate environment) using the camera. It is also possible to adapt pre-operative data which changes on the basis of the instrument's use, if for example tissue is removed using the instrument. Using this approach, it is possible to quantify the volume of soft tissue removed (for example using image processing techniques), and these quantifications can likewise be used, together with the corresponding 3D positions, to perform the elastic image registrations already mentioned above, for in this case, too, the quantifications can augment low-quality intra-operative virtual data (ultrasound, CT, low-field MR) with additional information, in order to provide better algorithm starting points and/or ancillary conditions for morphing methods, such as have already been explained above.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. An image output method for medical navigation in which the positional relationship of a trackable instrument with respect to a part of a patient's body is ascertained, and in which the trackable instrument and the part of the patient's body are displayed in real time in the correct positional relationship on an image output, the method comprising:
    displaying in real time the part of the patient's body based on virtual image data captured via a medical imaging method and on actual images captured in real time during navigation
    wherein the virtual image data is displayed on the image output as the primary basis of the image and the actual images captured in real time are correlated with and added into the virtual images as the secondary basis of the image so as to augment the virtual images, wherein the actual images are confined to at least one continuous area of the image output that constitutes less than 50% of the overall area of the image output assembled by the virtual image data and the actual images, and wherein capturing the actual images comprises capturing the actual images using a video image capture unit arranged on the trackable instrument.

2. The method according to claim 1, wherein displaying the part of the patient's body comprises weighting the virtual image data is more heavily than the actual images.

3. The method according to claim 1, wherein capturing the virtual image data comprises capturing image data before or during navigation using at least one of computed tomography, magnetic resonance tomography, an x-ray recording or fluoroscopic recording, a PET or SPECT recording.

4. The method according to claim 1, wherein capturing the actual images comprises capturing images which can be visually captured.

5. The method according to claim 4, wherein capturing the actual images comprises capturing images which correspond to an actual view of a region of interest.

6. The method according to claim 4, wherein capturing the actual images comprises capturing images by video capture apparatuses or by an object lens said actual images being captured in real time.

7. The method according to claim 1, wherein capturing the actual images comprises using a microscope or an endoscope to capture the actual images.

8. The method according to claim 1, wherein using the video image capture unit comprises using a camera or a camera light recorder as the video image capture unit.

9. The method according to claim 1, further comprising using a medical treatment instrument as the instrument.

10. The method according to claim 9, wherein using the medical treatment instrument as the instrument includes using a pointer, a pair of tweezers, a scalpel or a clamp as the medical instrument.

11. The method according to claim 1, further comprising using an instrument which is equipped for medical navigation as the instrument.

12. The method according to claim 11, wherein using an instrument equipped for medical navigation includes using an instrument which can be positionally detected by means of a tracking system.

13. The method according to claim 11, wherein using an instrument equipped for medical navigation includes using an instrument that includes a tracking reference.

14. The method according to claim 1, further comprising using an instrument which is pre-calibrated for navigation with a navigation system.

15. The method according to claim 1, further comprising using a plurality of instruments each provided with a video image capture unit, wherein the actual image data obtained from the respective plurality of instruments is used to reciprocally observe or monitor the other instruments and/or to produce supplemental images.

16. The method according to claim 1, further comprising:
using the video image capture unit to detect non-visible light wavelengths; and
using the captured non-visible light for image optimization.

17. The method according to claim 1, further comprising using the combination of the virtual image data and the actual images to positionally register the virtual image data.

18. The method according to claim 17, wherein using the combination of the virtual image data and the actual images to positionally register the virtual image data includes using the combination of virtual image data and actual image data for elastic image data registration.

19. The method according to claim 1, further comprising using the combination of the virtual image data and the actual images to update the virtual image data.

20. The method according to claim 1, further comprising weighting and testing for relevance image information used for assembling the image to be output and omitting less important image constituents from the image and/or intensifying or highlighting more important image constituents in the image.

21. A non-transitory computer readable medium comprising computer executable instructions adapted to perform a method in accordance with claim 1.

22. An image generating and image output device for medical navigation in which the positional relationship of a trackable instrument with respect to a part of a patient's body is ascertained, comprising:
an image output on which the trackable instrument and the part of the patient's body are displayed in the correct positional relationship;
an image processor which generates in real time a display of the part of the patient's body on the basis of virtual image data captured via a medical imaging method and on the basis of actual images captured in real time during navigation,
a video image capture unit configured to be arranged on the trackable instrument, said video image capture unit configured to provide the actual images; and
an image display control which displays the virtual image data on the image output as the primary basis of the image, wherein the actual images are correlated with and added into the virtual image data as the secondary basis of the image so as to augment the virtual images, wherein the actual images are confined to at least one continuous area of the image output that constitutes less than 50% of the overall area of the image output assembled by the virtual image data and the actual images.

23. The method according to claim 1, wherein the actual images are confined to the area that constitutes less than 30% of the overall area of the image output.

24. The method according to claim 1, wherein the actual images are confined to the area that constitutes less than 10% of the overall area of the image output.

* * * * *